United States Patent [19]

Hartman et al.

[11] Patent Number: 5,334,596
[45] Date of Patent: Aug. 2, 1994

[54] FIBRINOGEN RECEPTOR ANTAGONISTS

[75] Inventors: George D. Hartman; Wasyl Halczenko, both of Lansdale; John D. Prugh, Chalfont, all of Pa.

[73] Assignee: Merck & Co., Inc., Rahway, N.J.

[21] Appl. No.: 62,510

[22] Filed: May 11, 1993

[51] Int. Cl.$^5$ ............... C07D 495/04; C07D 491/048
[52] U.S. Cl. ........................... 514/301; 514/302; 546/114; 546/116
[58] Field of Search ............... 514/301, 302; 546/114, 546/116

[56] References Cited

U.S. PATENT DOCUMENTS

| | | | |
|---|---|---|---|
| 4,064,255 | 12/1977 | Champseix et al. | 424/267 |
| 4,122,255 | 10/1978 | Krapcho | 542/421 |
| 4,243,807 | 1/1981 | Friebe et al. | 546/232 |
| 4,313,947 | 2/1982 | Nakagawa et al. | 424/248.54 |
| 4,622,331 | 11/1986 | Jozic | 514/331 |
| 5,026,700 | 6/1991 | Harrison | 546/114 |
| 5,030,654 | 7/1991 | Barnish et al. | 514/510 |
| 5,064,814 | 11/1991 | Klein et al. | 514/18 |
| 5,190,938 | 3/1993 | Badorc | 546/114 |
| 5,204,469 | 4/1993 | Descamps | 546/114 |
| 5,252,581 | 10/1993 | Effland | 546/114 |
| 5,260,261 | 11/1993 | Prisbylla | 546/114 |

FOREIGN PATENT DOCUMENTS

| | | |
|---|---|---|
| 0229391A1 | 7/1987 | European Pat. Off. . |
| 0352249A1 | 1/1990 | European Pat. Off. . |
| 0372486A2 | 6/1990 | European Pat. Off. . |
| 0381033A1 | 8/1990 | European Pat. Off. . |
| 0384362A2 | 8/1990 | European Pat. Off. . |
| 0405537A | 2/1991 | European Pat. Off. . |
| 0478328A1 | 1/1992 | European Pat. Off. . |
| 0478362A2 | 1/1992 | European Pat. Off. . |
| 0478363A2 | 1/1992 | European Pat. Off. . |
| 0479481A2 | 8/1992 | European Pat. Off. . |

*Primary Examiner*—C. Warren Ivy
*Assistant Examiner*—D. Margaret M. Mach
*Attorney, Agent, or Firm*—Richard S. Parr; Melvin Winokur; Paul D. Matukaitis

[57] ABSTRACT

Fibrinogen receptor antagonists having the formula

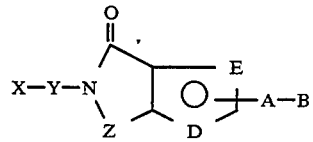

for example

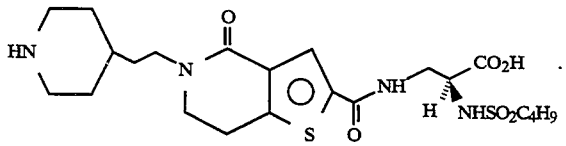

18 Claims, No Drawings

FIBRINOGEN RECEPTOR ANTAGONISTS

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in Science, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in Proc. Nat'l Acad. Sci. U.S.A., 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in J. of Biol. Chem., 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between nonterminal residues Pen and Cys, rendered the peptide much less effective at inhibiting attachment to fibronectin.

In Proc. Nat'l Acad. Sci. U.S.A., 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., Proc. Nat'l Acad. Sci. U.S.A., 83,5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., Biochem. 23, 1767–1774 (1984); Ginsberg et al., J. Biol. Chem. 260(7), 3931–3936 (1985); and Haverstick et al., Blood 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., J. Biol Chem., 262, 16157–16163 (1987); Huang et al., Biochemistry 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., J. Biol. Chem., 263, 19827–19832 (1988). See also, Dennis et. al., Proc. Nat'l Acad. Sci. USA, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No. 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. The application PCT/US90/02746 describes the use of antibody-polypeptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a thioether linkage in the cycle. The application PCT/US90/05367 published May 2, 1991 also discloses the use of peptides and pseudopeptides such as N-amidino-piperidine-3-carboxylglycyl-L-aspartyl-L-valine that inhibit platelet aggregation and thrombus formation in mammalian blood.

The application Eur. Pat. App. No. 91103462.7 discloses linear compounds which can include internal piperazinyl or piperidinyl derivatives. Eur. Pat. App. No. 91300179.8, assigned to Merck & Co., Inc., and published on Jul. 17, 1991 discloses linear polypeptide fibrinogen receptor antagonists. Eur. Pat. App. No. 90101404.3 discloses compounds of the $R^1$—A—(W-)$_a$—X—(CH$_2$)$_b$—(Y)$_c$—B—Z—COOR wherein $R^1$ is a guandidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

The invention is a fibrinogen receptor antagonist of the formula:

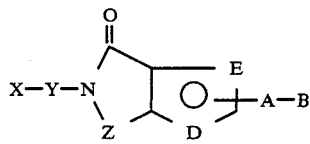

for example

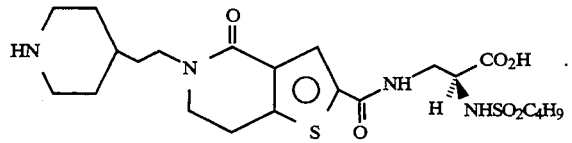

DETAILED DESCRIPTION OF THE INVENTION

The present invention includes compounds having the formula

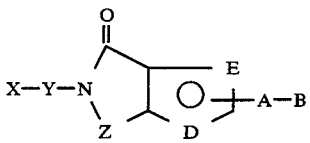

and pharmaceutically acceptable salts, wherein
X is chosen from

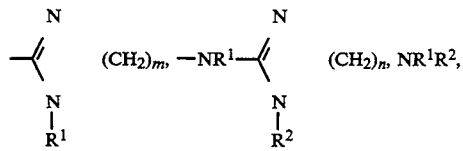

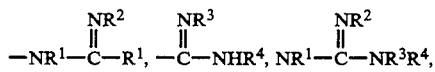

or a 4- to 10-membered mono- or polycyclic aromatic or nonaromatic mono- or polycyclic ring system containing 0, 1, 2, 3 or 4 heteroatoms selected from N, O and S and either unsubstituted or substituted with $R^1$, $R^2$, $R^3$ or $R^4$, wherein $R^1$, $R^2$, $R^3$ and $R^4$ are independently selected from the group consisting of hydrogen,
$C_{1-10}$ alkyl,
aryl $C_{0-8}$ alkyl,
oxo,
thio,
amino $C_{0-8}$ alkyl, $C_{1-3}$ acylamino $C_{0-8}$ alkyl,
$C_{0-6}$ alkylamino $C_{0-8}$ alkyl,
$C_{1-6}$ dialkylamino $C_{0-8}$ alkyl,
$C_{1-4}$ alkoxy $C_{0-6}$ alkyl,
carboxy $C_{0-6}$ alkyl, $C_{1-3}$ alkoxycarbonyl $C_{0-6}$ alkyl,
carboxy $C_{0-6}$ alkyloxy, and
hydroxy $C_{0-6}$ alkyl,
where m and n are integers from 2–5;
Y and A are independently chosen from:

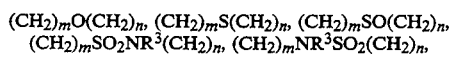

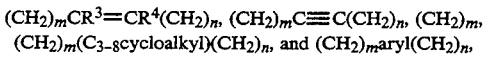

where aryl represents a 5- or 6-membered aromatic ring system containing 0, 1, 2 or 3 heteroatoms chosen from N, O and S and either unsubstituted or substituted with $R_1$, and where m and n are integers independently chosen from 0–6;
Z is chosen from:

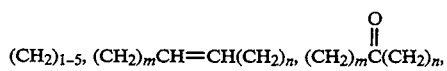

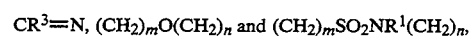

where m and n are integers independently chosen from 0–6;
D and E are independently chosen from C, N, O and S;
B is chosen from

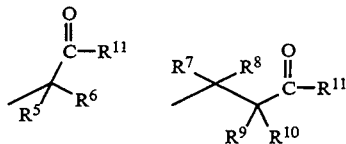

where $R^5$, $R^6$, $R^7$, $R^8$, $R^9$ and $R^{10}$ are independently chosen from: hydrogen, fluorine, $C_{1-8}$ alkyl, hydroxyl, hydroxy $C_{1-6}$ alkyl, carboxy $C_{0-6}$ alkyl,
$C_{1-6}$ alkyloxy, $C_{1-6}$ alkylcarbonyl, aryl $C_{0-6}$ alkylcarbonyl,
$C_{1-6}$ alkylcarbonyloxy, aryl $C_{0-6}$ alkylcarbonyloxy, $C_{1-6}$ alkylaminocarbonyloxy, aryl $C_{0-6}$ alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl,
aryl $C_{0-6}$ alkylthiocarbonylamino $C_{0-6}$ alkyl,
wherein groups may be unsubstituted or substituted with one or more substituents selected from $R^1$ and $R^2$, and

where G is an L- or D-amino acid, or its corresponding ester, connected through an amide linkage;
$R^{11}$ is chosen from
hydroxy,
$C_{1-8}$ alkyloxy,
aryl $C_{0-6}$ alkyloxy,
$C_{1-8}$ alkylcarbonyloxy $C_{1-4}$ alkyloxy,
aryl $C_{0-8}$ alkylcarbonyloxy $C_{1-4}$ alkyloxy, or
an L- or D-amino acid joined by an amide linkage and wherein the carboxylic acid moiety of said amino acid is as the free acid or is esterified by $C_{1-6}$ alkyl.

A preferred embodiment of the present invention are compounds having the structure

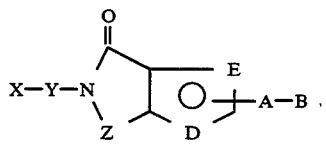

and pharmaceutically acceptable salts thereof wherein
X is chosen from

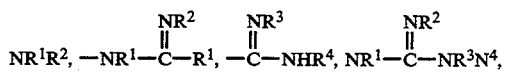

or a 4- to 10-membered mono- or polycyclic aromatic or nonaromatic mono- or polycyclic ring system containing 0, 1, 2, 3 or 4 heteroatoms selected from N, O and S and either unsubstituted or substituted with R1, R2, R3, or R4,
wherein $R^1$, $R^2$, $R^3$ and $R^4$ are independently selected from the group consisting of hydrogen,
$C_{1-10}$ alkyl,
aryl $C_{0-8}$ alkyl,
oxo, and
thio;
Y and A are independently chosen from:

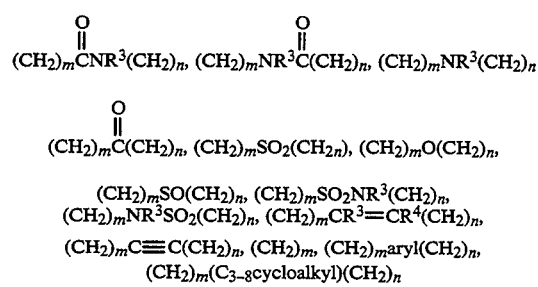

where aryl represents a phenyl or thiophene ring either unsubstituted or substituted with $R^1$, and where m and n are integers independently chosen from 0–6;
Z is chosen from:

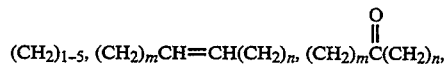

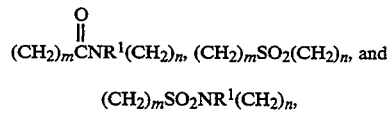

where m and n are integers independently chosen from 0–6, and D and E are independently chosen from C, N, O and S;
B is chosen from

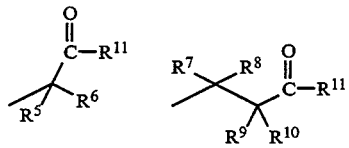

where $R^5$, $R^6$, $R^7$, $R^8$, $R^9$ and $R^{10}$ are independently chosen from: hydrogen, fluorine,
$C_{1-8}$ alkyl, hydroxyl, hydroxy $C_{1-6}$ alkyl, carboxy $C_{0-6}$ alkyl,
$C_{1-6}$ alkyloxy, $C_{1-6}$ alkylcarbonyl, aryl $C_{0-6}$ alkylcarbonyl,
$C_{1-6}$ alkylcarbonyloxy, aryl $C_{0-6}$ alkylcarbonyloxy, $C_{1-6}$alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl, $C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl,
aryl $C_{0-6}$ alkylthiocarbonylamino $C_{0-6}$ alkyl,
wherein groups may be unsubstituted or substituted with one or more substituents selected from $R^1$ and $R^2$, and

where G is an L- or D-amino acid, or its corresponding ester, connected through an amide linkage;

$R^{11}$ is chosen from
hydroxy,
$C_{1-8}$ alkyloxy,
aryl $C_{0-6}$ alkyloxy,
$C_{1-8}$ alkylcarbonyloxy $C_{1-4}$ alkyloxy, and
aryl $C_{1-8}$ alkylcarbonyloxy $C_{1-4}$ alkyloxy.

A more preferred embodiment of the present invention are compounds having the structure

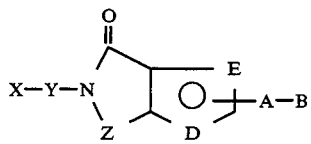

and pharmaceutical salts thereof wherein
X is chosen from

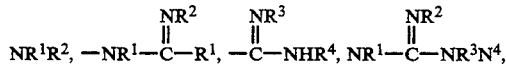

or a 4- to 10-membered mono- or polycyclic aromatic or nonaromatic mono- or polycyclic ring system containing 0, 1, 2, 3 or 4 heteroatoms selected from N, O and S and either unsubstituted or substituted with $R^1$, $R^2$, $R^3$ or $R^4$, wherein $R^1$, $R^2$, $R^3$ and $R^4$ are independently selected from the group consisting of hydrogen, $C_{1-10}$ alkyl, and aryl $C_{0-8}$ alkyl;

Y and A are independently chosen from:

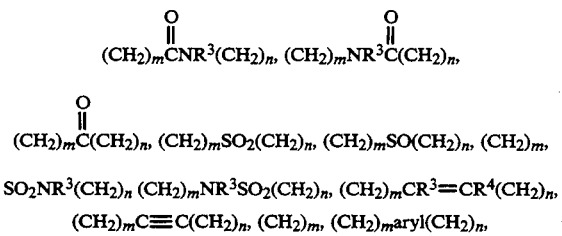

where aryl represents a phenyl or thiophene ring either unsubstituted or substituted with $R^1$, and where m and n are integers independently chosen from 0-6;

Z is chosen from:

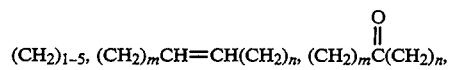

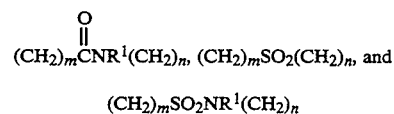

where m and n are integers independently chosen from 0-6;

D and E are independently chosen from C and S;

B is chosen from

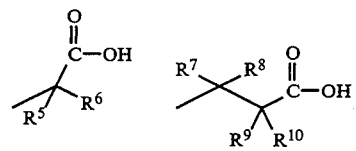

where $R^5$, $R^6$, $R^7$, $R^8$, $R^9$ and $R^{10}$ are independently chosen from: hydrogen, fluorine,
$C_{1-8}$ alkyl, hydroxyl, hydroxy $C_{1-6}$ alkyl, carboxy $C_{0-6}$ alkyl,
$C_{1-6}$ alkyloxy, $C_{1-6}$ alkylcarbonyl, aryl $C_{0-6}$ alkylcarbonyl,
$C_{1-6}$ alkylcarbonyloxy, aryl $C_{0-6}$ alkylcarbonyoxy,
$C_{1-6}$ alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl, $C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl, and
aryl $C_{0-6}$ alkylthiocarbonylamino $C_{0-6}$ alkyl.

The term "pharmaceutically acceptable salts" shall mean non-toxic salts of the compounds of this invention which are generally prepared by reacting the free base with a suitable organic or inorganic acid. Representative salts include the following salts: Acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

The term "alkyl" means straight or branched alkane, alkene or alkyne.

The term "alkoxy" includes an alkyl portion where alkyl is as defined above.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit.

The term "halogen" includes fluorine, chlorine, iodine and bromine.

The term "oxy" means an oxygen (O) atom. The term "thio" means a sulfur (S) atom. Under standard nomenclature used throughout this disclosure, the terminal portion of the designated side chain is described first followed by the adjacent functionallity toward the point of attachment. For example, a $C_{1-6}$ alkyl substituted with $C_{1-6}$ alkylcarbonylamino is equivalent to

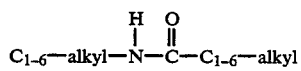

In the schemes and examples below, various reagent symbols have the following meanings:
BOC (or Boc); t-butyloxycarbonyl.
Pd-C: Palladium on activated carbon catalyst.
DMF: Dimethylformamide.
DMSO: Dimethylsulfoxide.
CBZ: Carbobenzyloxy.
$CH_2Cl_2$: Methylene chloride.
$CHCl_3$: chloroform.
EtOH: ethanol.
MeOH: methanol.
EtOAc; ethyl acetate.
HOAc: acetic acid.
BOP: Benzotriazol-1-yloxytris(dimethylamino)phosphonium, hexafluorophosphate.
EDC: 1-(3-Dimethylaminopropyl)-3-ethylcarbodiimide hydrochloride
Oxone: potassium peroxymonosulfate
LDA: Lithium diisopropylamide The compounds of the present invention can be administered in such oral froms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramusculsar form, all using forms well known to those of ordinary skill in pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., *Amer. J. Physiol.*, 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarilly skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–100 mg/kg/day and most preferably 0.01–20 mg/kg/day. Intravenously, the most preferred doses will range from about 1 to about 10 mg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those or ordinary skill in that art. To be administered in the form of a transdermal delivery system, the dosage administration will, or course, be continuous rather that intermittant throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, nontoxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, cornsweeteners, natural and synthetic gums such as acacia, tragacanth or sodium alginate, carboxymethylkcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug cariers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be coadministered with suitable anticoagulation agents or thrombolytic agents such as plasminogen activators or streptokinase to achieve synergistic effects in the treatment of various vascular pathologies. They may also be combined with heparin, aspirin, or warfarin.

Prefered compounds of the invention are selected from the group consisting of:

| | IC$_{50}$ ($\mu$M) |
|---|---|
| [structure: HN-piperidine-(CH$_2$)$_2$-N-fused bicyclic with thiophene, C(=O)NH-CH(CH$_3$)-CO$_2$H] | 0.22 |
| [structure: HN-piperidine-(CH$_2$)$_2$-N-fused bicyclic with thiophene, C(=O)NH-CH$_2$CH$_2$-CO$_2$H] | 0.15 |
| [structure: HN-piperidine-(CH$_2$)$_2$-N-fused bicyclic with thiophene, C(=O)-(CH$_2$)$_3$CO$_2$H] | 0.26 |

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$ (1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The IC$_{50}$ is the dose of a particular compound inhibiting aggregation by 50% relative to a control lacking the compound.

The novel compounds of the present invention were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celcius unless otherwise noted.

In addition to the following preparative procedures, several examples of in-vitro bioactivity of compounds within the scope of the present invention are indicated. To illustrate, one test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Reagents 1-2 and 2-2 used in the following examples are prepared according to the following procedure:

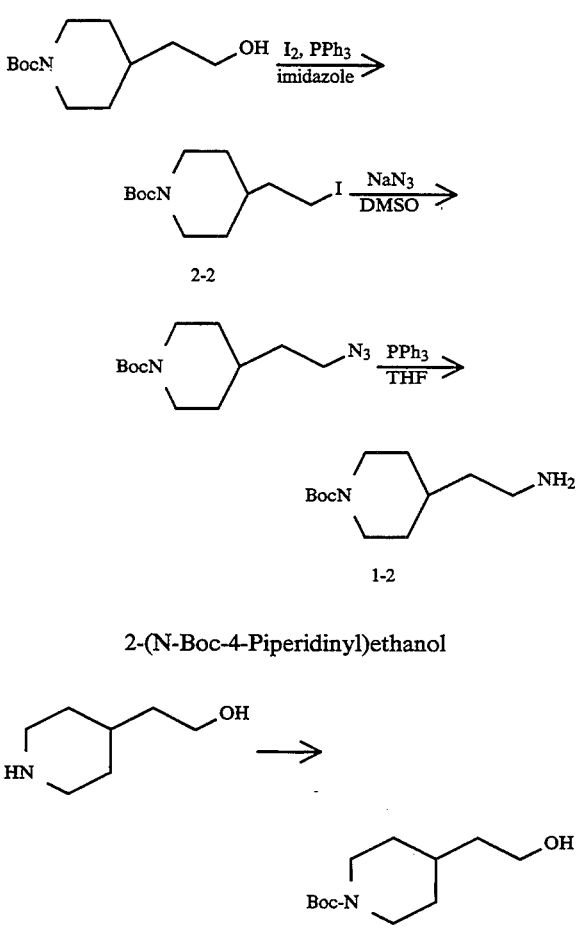

2-(N-Boc-4-Piperidinyl)ethanol

4-Piperidine-2-ethanol (Aldrich) (130 g, 1.0 mole) was dissolved in 700 mL dioxane, cooled to 0° C. and treated with 3N NaOH (336 mL, 1.0 mole), and di-t-butyldicarbonate (221.8 g, 1.0 mole). The ice bath was removed and the reaction was stirred overnight. The reaction was concentrated, diluted with water and extracted with ether. The ether layers were combined, washed with brine, dried over MgSO4, filtered and evaporated to give the desired product. $R_f=0.37$ in 1:1 EtOAc/Hexanes, ninhydrin stain $^1$H NMR (300 MHz, CDCl$_3$) δ4.07 (bs, 2H), 3.7 (bs, 2H), 2.7 (t, J=12.5 Hz, 2H), 1.8-1.6 (m, 6H), 1.51 (s, 9H), 1.1 (ddd, J=4.3, 12.5, 12 Hz, 2H).

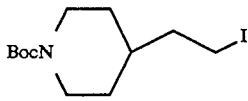

2-2

2-(N-Boc-4-Piperidinyl)ethyl iodide(2—2)

2-(N-Boc-4-piperidinyl)ethanol (10.42 g, 0.048 mole was dissolved in 400 ml benzene and imidazole (4.66 g, 0.068 moles), triphenylphosphine (15.24 g, 0.05 moles) and iodine (0.052 moles) were added at room temperature. After 6 hours the reaction mixture was filtered and the filtrate was evaporated to give a dark residue. This was purified by flash chromatography on silica gel eluting with 10% EtOAc-hexanes to give 2—2 as a yellow oil.

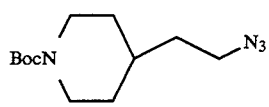

2-(N-Boc-4-Piperidinyl)ethylazide

To 2—2 (27.9 g, 0.082 moles)dissolved in DMSO (400 ml) was added sodium azide (5.01 g, 0.086 moles) at room temperature and the resulting solution was heated at 65° for 2 hours. The cooled reaction mixture was diluted with 250 ml EtOAc, washed with 2×100 ml portions of water 2×50 ml portions of brine and then dried (MgSO4). Solvent removal provided the desired product as a pale yellow oil, $R_f$ 0.5 (silica gel, 70% acetone/hexane).

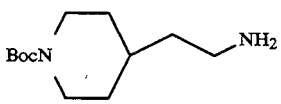

1-2

2-(N-Boc-4-Piperidinyl)ethylamine (1-2)

To a solution of 2-(N-Boc-4-piperidinyl)ethylazide (19.3 g, 0.076 moles) in THF (400 ml)/H2O (195 ml) was added triphenylphosphine (80.0 g, 0.305 moles) in one portion at room temperature. This was stirred at room temperature 3 hours and the organic solvents were then removed in vacuo. The residue was acidified to pH 2 with 10% KHSO4 solution and this was extracted 4×100 ml portions of EtOAc. The organic extract was extracted with 2×100 ml portions of 10% KHSO4 and the aqueous phases were combined and the pH was adjusted to 10 with 2N NaOH. This solution was extracted with 4×200 ml portions of CH2Cl2. These were combined, dried (MgSO4) and the solvent was removed to give 1-2 as an oil. $R_f$0.3 (silica gel, eluting with 10% CH3OH in CHCl3/NH3).

$^1$H NMR (300 MHz, CDCl$_3$) δ4.05 (broad, 2H), 2.72 (t, J=7.2 Hz, 2H), 2.62 (m, 2H), 1.64 (d, J=12.2 Hz, 2H), 1.43 (s, 9H), 1.42-1.32 (m, 5H), 1.09 (m, 2H).

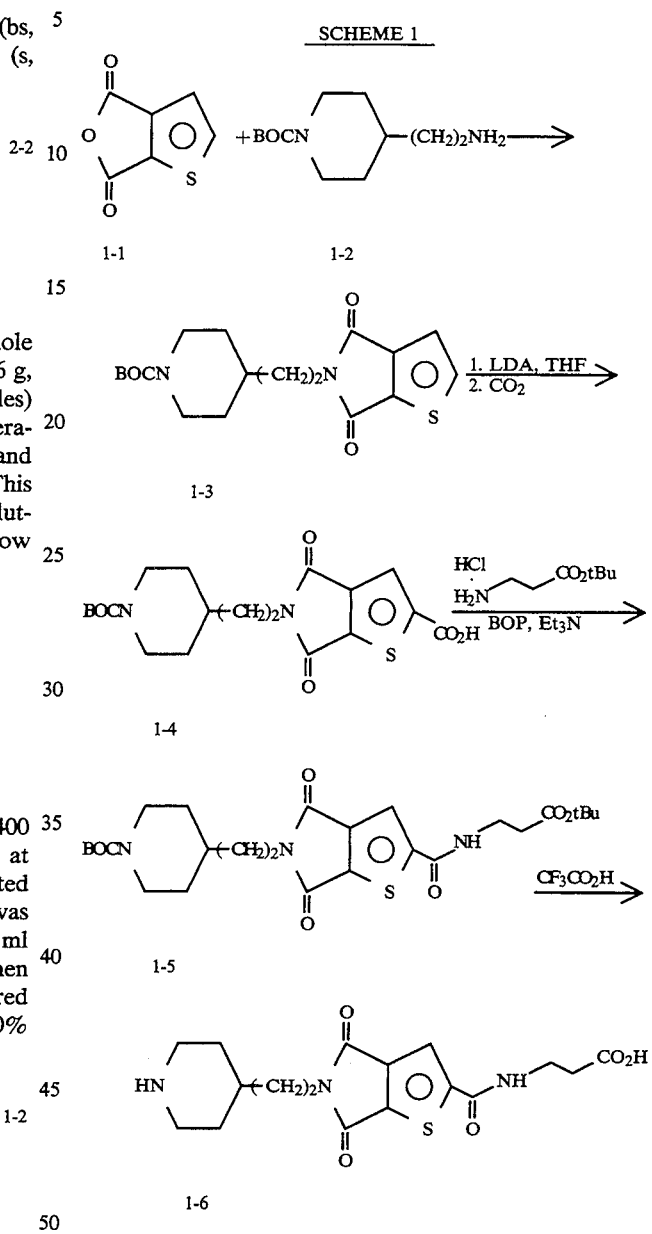

N-[2-(N'-Boc-4-Piperidinyl)ethyl]-2,3-thiophenedicarboximide (1-3)

A solution of 2,3-thiophenedicarboxylic acid anhydride (Aldrich) (0.15 g, 1.0 mmoles) in pyridine (2 ml) was treated with 2(N-t-Boc-4-piperidinyl)ethylamine (1-2) (0.23 g, 1.0 mmoles) and this solution was heated at 100° for 20 hrs. The cooled reaction mixture was diluted with H2O (35 ml), acidified to pH 2-3 with KHSO4 and extracted with EtOAc. The organic phase was dried (MgSO4), concentrated and the residue was dissolved in THF, treated with carbonyldiimidazole (CDI) (Aldrich) (0.16 g, 1.0 mmoles). After heating at 65° for 3 hours, the cooled reaction mixture was diluted with EtOAc, extracted with 1N KHSO4 solution H2O, saturated NaHCO3, brine and the organic phase was dried (MgSO4) and concentrated to give 1-3.

$^1$H NMR (300 MHz, CDCl$_3$) δ1.14 (2H, m), 1.45 (9H, S), 1.60 (3H, m), 1.76 (2H, bd), 2.68 (2H, dt), 3.64 (2H, t), 4.09 (2H, bd), 7.31 (1H, d), 7.77 (1H, d).

5-Carboxy-[N-2-(N'-Boc-4-Piperidinyl)ethyl]-2,3-thiophenedicarboximide (1-4)

A solution of 1-3 (1.07 g, 2.84 mmoles) in THF (20 ml) at −100° was treated with LDA (2.94 mmoles) and after stirring for 10 minutes at −100°, the reaction mixture was poured into a CO$_2$/ether slurry. This mixture was stirred and allowed to warm to room temperature over 2 hours. The reaction mixture was concentrated and treated with 1N KHSO$_4$ solution and extracted with EtOAc, dried and concentrated. The residue was purified by flash chromatography on silica gel eluting with MeOH/AcOH/CHCl$_3$ (5:5:90) to provide 1-4.

$^1$H NMR (300 MHz, CDCl$_3$) δ1.13 (2H, m), 1.45 (9H, S), 1.53 (3H, m), 1.76 (2H, m), 2.65 (2H, m), 3.62 (2H, m), 4.10 (2H, m), 8.07 (1H, s).

5-(2-t-Butyloxycarbonylethyl)carboxamide-[N-2-(N'-Boc-4-piperidinyl)ethyl]-2,3-thiophenedicarboximide (1-5)

A solution of 1-4 (0.034 g, 0.07 mmoles) in CH$_3$CN (1 ml) was treated with BOP (0.037 g, 0.085 mmoles), β-alanine t-butylester HCl (0.015 g, 0.085 mmoles), an Et$_3$N (0.026 mmoles) at room temperature and the resulting solution was stirred for 20 hours. The solvent was removed and the residue was taken up in EtOAc, extracted with H$_2$O, 1N KNSO$_4$, saturated NaHCO$_3$, brine, dried (MgSO$_4$) and concentrated. The residue was purified by flash chromatography on silica gel eluting with 40% EtOAc/hexanes to give pure 1-5.

$^1$H NMR (300 MHz, CDCl$_3$) δ1.15 (2H, m), 1.45 (9H, S), 1.48 (9H, S), 1.62 (3H, m), 1.76 (2H, bd), 2.58 (2H, t), 2.66 (2H, dt), 3.67 (3H, m), 4.09 (2H, bd), 7.56 (1H, S).

5-(2-Carboxyethyl)carboxamide-[N-2-(4-Piperidinyl)ethyl]-2,3-thiophenedicarboximide (1-6)

A solution of 1-5 in CH$_2$Cl$_2$ was treated at room temperature with CF$_3$CO$_2$H and this was stirred for 3 hours. The reaction mixture was concentrated and 1-6 was obtained by preparative hplc.

$^1$H NMR (300 MHz, CD$_3$OD) δ1.39 (2H, m), 1.64 (3H, m), 2.04 (2H, bd), 2.63 (2H, t), 2.93 (2H, t), 3.62 (2H, m), 7.87 (1H, S).

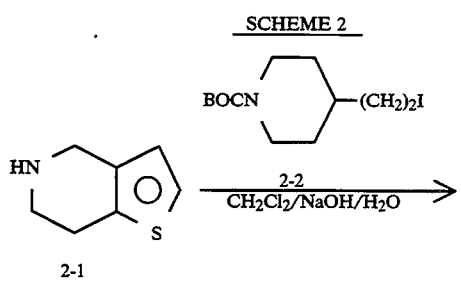

SCHEME 2

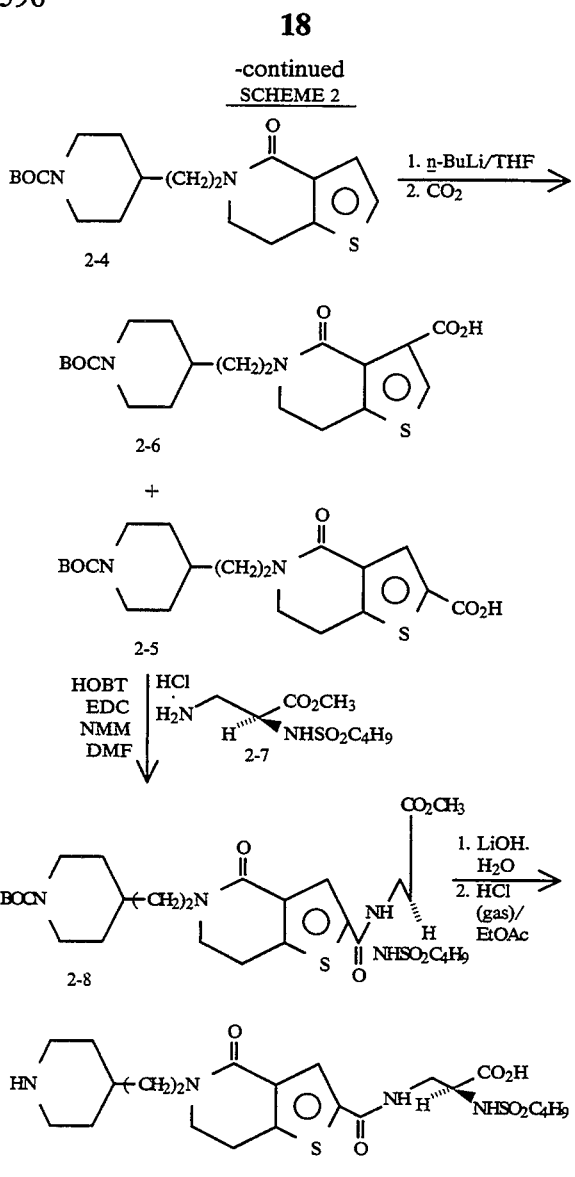

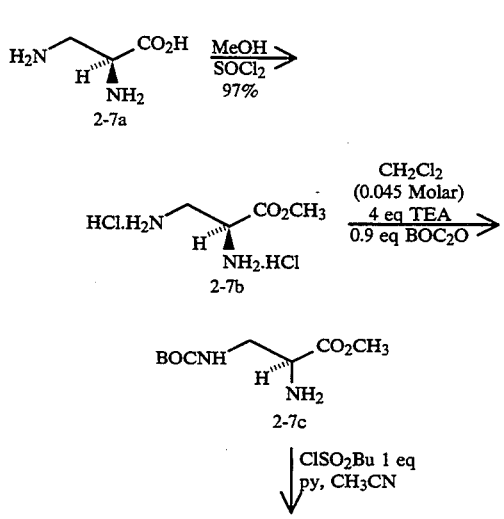

Preparation of 2(S)-(n-Butylsulfonylamino)-3-aminopropionic acid methyl ester hydrochloride (2-7)

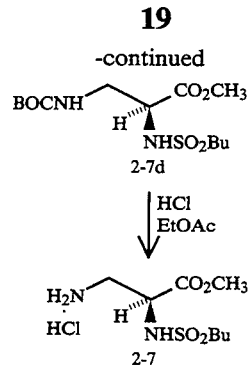

2(S),3-Diaminopropionic acid methyl ester (2-7b)

Methanol (400 mL) was cooled to 0° C. and thionyl chloride (217 mL, 3.0 moles, 20 eq) was added dropwise under argon. After addition was completed, the solution was warmed to room temperature for 20 minutes. 2(S), 3-Diaminopropanoic acid (Schweizerhall) (20 g, 0.243 mole) was crushed to a fine powder and added to the solution. The reaction was heated to reflux for 48 hours, at which time TLC showed a small amount of starting material remaining. An additional portion of methanol (100 mL) and thionyl chloride (72 mL) was prepared as before and added to the reaction at room temperature; the reaction was then stirred overnight at room temperature. The reaction was worked up by removal of solvent at 40° C. in vacuo, to provide 2-7b. $R_f$ 0.72 (9:1:1 EtOH/H$_2$O/NH$_4$OH).

$^1$H NMR (400 MHz, D$_2$O) δ4.55 (dd, J=5.4, 8.2 Hz, 1H), 3.92 (s, 3H), 3.64 (dd, J=8.2, 13.8 Hz, 1H), 3.55 (dd, J=5.4, 13.8 Hz, 1H).

2(S),-3(N-t-Butyloxycarbonyl)diaminopropionic acid methyl ester (2-7c)

2-7b (6.0 g, 31.5 mmoles) was crushed to a fine powder, suspended in 1L of CH$_2$Cl$_2$ and cooled to −78° C. under argon. Triethylamine (17.5 mL, 0.126 moles, 4 eq) was added dropwise; the solution gradually became homogenous. Di-t-butyldicarbonate (6.18 g, 2.83 mmoles, 0.9 eq) was dissolved in 50 mL CH$_2$Cl$_2$ and added dropwise to the solution. After the addition was completed, the reaction was placed in an ice bath and stirred for 1½ hours. The reaction was transferred to a separatory funnel and extracted with 3×50 mL of 10% KHSO$_4$ solution. The aqueous layer was washed with 3×10 mL of CH$_2$Cl$_2$, then basified with saturated NaHCO$_3$ and 3N NaOH solution to pH10 and extracted with 10×100 mL of CH$_2$Cl$_2$. The organic layer was dried with Na$_2$SO$_4$, filtered and evaporated to give crude 2-7c. Column chromatography in 2.5% MeOH-/EtOAc gave 2-7c as an oil. $R_f$ 0.39 (5% MeOH-/EtOAc).

$^1$H NMR (400 MHz, CDCl$_3$) δ5.0 (bs, 1H), 3.72 (s, 3H), 3.56 (t, J=5.7 Hz, 1H), 3.46 (m, 1H), 3.23 (m, 1H), 1.55 (bs, 2H), 1.42 (s, 9H).

2(S)-(n-Butylsulfonylamino)-3-(N-t-butyloxycarbonylamino)propionic acid methyl ester (2-7d)

2-7c was dissolved in acetonitrile (100 mL) and three portions of n-butylsulfonyl chloride (1.62 mL, 12.5 mmoles, 1.1 eq each) and pyridine (1.0 mL, 12.5 mmoles, 1.1 eq each) were added over a period of three hours. The reaction was allowed to stir overnight, concentrated to ¼ its original volume, then diluted with 100 mL EtOAc and washed with 10% KHSO$_4$ (5×20 mL), dried with brine and MgSO$_4$, filtered and evaporated.

Column chromatography in 20%–40% EtOAc/hexanes gave 2-7d as an oil. $R_f$ 0.6 (5% MeOH/CHCl$_3$).

$^1$H NMR (400 MHz, CDCl$_3$) δ5.48 (bd, 1H), 4.9 (bs, 2H), 4.22 (m, 1H), 3.8 (s, 3H), 3.53 (m, 2H), 3.02 (m, 2H), 1.80 (m, 2H), 1.46 (m, 2H), 1.43 (s, 9H), 0.94 (t, J=7.4 Hz, 3H).

2(S)-(n-Butylsulfonylamino)-3-aminopropionic acid methyl ester hydrochloride (2-7)

2-7d (2.0 g, 5.9 mmoles) was dissolved in 30 mL of EtOAc and cooled to −40° C. HCl gas was bubbled through the solution until it was saturated, the reaction was warmed to 0° C. and stirred for 1 hour. The excess HCl was removed under vaccum at room temperature and the reaction was concentrated at 35° C. to give 2-7. $R_f$ 0.6 (9:1 EtOH/H$_2$O).

$^1$H NMR (400 MHz, CDCl$_3$) δ8.1 (bs, 2H), 7.2 (m, 1H), 4.65 (m, 1H), 3.82 (s, 3H), 3.65 (m, 1H), 3.54 (m, 1H), 3.20 (bs, 2H), 1.8 (m, 2H), 1.45 (m, 2H), 0.95 (t, J=7.3 Hz).

5-[2-(N-BOC-4-Piperidinyl)ethyl]-4,5,6,7-tetrahydrothieno[3,2-c]pyridine (2-3)

A suspension of 4,5,6,7-tetrahydrothieno[3,2-c]pyridine.HCL (2-1) (1.76 g, 0.01 moles) in CH$_2$Cl$_2$ (15 ml) was treated with 2-(N-BOC-4-piperidinyl)ethyl iodide (2—2) (3.73 g, 0.011 moles) followed by 20% NaOH (10 ml) and Aliquot-336 (Aldrich). After stirring for 20 hours the reaction mixture was diluted with CH$_2$Cl$_2$ and the organic phase was separated, washed with brine, dried (Na$_2$SO$_4$) and concentrated. The residue was purified by flash chromatography on silica gel eluting with CHCl$_3$ (98)/MeOH(2) to give pure 2-3.

$^1$H NMR (300 MHz), CDCl$_3$) δ1.16 (2H, m), 1.45 (9H, S), 1.55 (3H,m), 1.69 (2H, bd), 2.57 (2H, m), 2.68 (2H, bt), 2.81 (2H, m), 2.90 (2H, m), 4.08 (2H, b), 6.81 (1H, d), 7.08 (1H, d).

4-Oxo-5-[2-(N-BOC-4-Piperidinyl)ethyl]-4,5,6,7-tetrahydrothieno[3,2-c]pyridine (2-4)

A solution of 2-3 (3.25 g, 0.0093 moles) in acetone (100 ml) was treated at room temperature with KMnO$_4$ (2.93 g, 0.0185 moles) and the resulting mixture was stirred for 1 hour. The mixture was then filtered (silica gel pad), concentrated and the residue purified by flash chromatography on silica gel eluting with EtOAc (2)/hexanes (3) to give pure 2-4 as an oil.

$^1$H NMR (300 MHz, CDCl$_3$) δ1.17 (2H, m), 1.45 (9H, S), 1.56 (3H, m), 1.75 (2H, m), 2.48 (2H, dt), 3.06 (2H, t), 3.56 (2H, m), 4.08 (2H, b), 7.09 (1H, d), 7.42 (1H, d).

2-Carboxy-4-Oxo-5-[2-(N-BOC-4-Piperidinyl)ethyl]-4,5,6,7-tetrahydrothieno[3,2-c]pyridine (2-5)

A solution of 2-4 (3.65 g, 0.01 moles) in THF (100 ml) was treated at −78° with n-BuLi (in hexane) and stirring was continued for 30 minutes. This was then poured into a slurry of Et$_2$O/CO$_2$ and this was stirred for 0.5 hours. A solution of 10% KHSO$_4$ was added, and after stirring for 10 minutes, the reaction mixture was diluted with H$_2$O. The organic phase was separated, washed with H$_2$O, brine, dried (Na$_2$SO$_4$) and concentrated. The residue was purified by flash chromatography on silica gel eluting with CHCl$_3$ (95)/MeOH(5) to give pure 2-5, $R_f$ 0.5.

$^1$H NMR (300 MHz, CDl$_3$) δ1.17 (2H, m), 1.45 (9H, s), 1.52 (3H, m), 1.72 (2H, bd), 2.69 (2H, bt), 3.12 (2H, t), 3.59 (2H, t), 3.68 (2H, t), 4.09 (2H, b), 7.28 (1H, s), 8.18 (1H, S).

An additional compound, 2–6 was obtained from this chromatography, $R_f$ 0.3; this compound was the 3-Carboxy analog of 2–5.

2-[3-(Methyl 2(S)-n-butylsulfonylamino)propionate]carboxamide-4-oxo-5-[2-(N-BOC-4-piperidinyl)ethyl]-4,5,6,7-tetrahydro[3,2-c]pyridine (2–8)

A solution of 2–5 (0.135 g, 0.44 mmoles) in DMF (20 ml) was treated with 2–7 (0.54 mmoles), HOBT (0.073 g, 0.54 mmoles), NMM (0.15 g, 1.47 mmoles), and EDC (0.107 g, 0.55 mmoles). After stirring for 20 hours, the solvent was removed and the residue taken up in $H_2O$ and this was extracted with EtOAc. The organic extract was washed with 10% $KHSO_4$, brine, saturated $NaHCO_3$, brine, dried ($NaSO_4$), concentrated and the residue purified by flash chromatography on silica gel eluting with $CHCl_3(95)/MeOH(5)$. $R_f$ 0.45 [silica, $CHCl_3(95)/MeOH/(5)$] to give pure 2–8.

$^1H$ NMR (300 MHz, $CDCl_3$) δ0.89 (3H, t), 1.15 (2H, m), 1.45 (9H, S), 1.55 (3H, m), 1.75 (2H, m), 2.68 (2H, t), 3.08 (3H, m), 3.54 (2H, t), 3.62 (2H, t), 3.80 (3H, S), 3.88 (1H, m), 4.08 (2H, bd), 4.38 (1H, m), 6.16 (1H, bd), 7.28 (1H, bt), 7.80 (1H, S), 8.02 (1H, bs).

2-[3-(2(S)-n-butylsulfonylamino)propionic acid]carboxamide-4-oxo-5-[2-(4-piperidinyl)ethyl]-4,5,6,7-tetrahydro[3,2-c]pyridine (2–9)

2–8 (0.3 g, 0.47 mmoles) was dissolved in $THF/MeOH/H_2O$ (1:1:1) (15 ml), treated with $LiOH·H_2O$ (0.06 g, 1.42 mmoles), and the resulting solution was stirred for 16 hours at room temperature. The solvent was removed and the residue was dissolved in $H_2O$ (100 ml), extracted with EtOAc and the organic phase was acidified (pH 2–3) with 10% $KHSO_4$ solution. This was extracted with EtOAc and the organic phase was washed with brine, dried ($Na_2SO_4$) and concentrated to give the desired acid as an oil. $R_f$ 0.1 (silica, $CH_3OH/CHCl_3/HOAc$ (5:95:1).

This oil was dissolved in EtOAc, cooled to −25° and treated with HCl gas for 15 minutes. The reaction flask was then stoppered and stirred for 1 hour at 0°. Solvent removal gave 2–9 as a white solid.

$^1H$ NMR (300 MHz, $CD_3OD$) δ0.89 (3H, t), 1.28–1.52 (4H, m), 1.52–1.90 (5H, m), 2.05 (2H, bd), 2.87–3.08 (4H, m), 3.12 (2H, t) 3.38 (2H, bd, 3.43–3.90 (6H, m), 4.30 (1H, dd) 7.85 (1H, s), 8.68 (0.75H, bt)

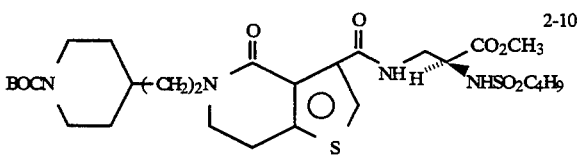

3-[3-(Methyl 2(S)-n-butylsulfonylamino)propionate]carboxamide-4-oxo-5-[2-(N-BOC-4-piperidinyl)ethyl]-4,5,6,7-tetrahydro[3,2-c]pyridine (2–10)

2–6 (0.245 g, 6.0 mmoles) in DMF (20 ml) was treated with 2–7 (6.0 mmoles), HOBT (0.9 g, 6.6 mmoles), EDC (0.144 g, 0.75 mmoles) and NMM (0.18 g, 1.8 mmoles) as described for 2–5 to provide crude 2–10. This was purified by flash chromatography on silica gel, eluting with $CHCl_3$ (95)/MeOH(5), $R_f$ 0.5, to give pure 2–10.

$^1H$ NMR (300 MHz, $CDCl_3$) δ0.90 (3H, t), 1.18 (2H, m), 1.25 (2H, m), 1.45 (9H, S), 1.57 (3H, m), 1.78 (4H, m), 2.70 (2H, bt), 3.06 (3H, m), 3.60 (3H, m), 3.79 (3H, S), 3.88 (1H, m), 4.10 (2H, b), 4.41 (1H, m), 6.02 (1H, d), (1H, S).

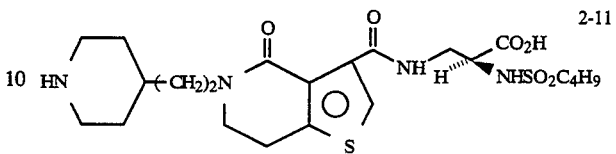

3-[3-(2(S)-n-Butylsulfonylamino)propionic acid]carboxamide-4-oxo-5-[2-(4-piperidinyl)ethyl]-4,5,6,7-tetrahydro[3,2-c]pyridine (2–11)

2–10 (0.15 g, 0.24 mmoles) was treated with $LiOH·H_2O$ as described for 2–8 to provide the desired acid. $R_f$ 0.25 [silica, $CHCl_3$ (95)/MeOH(5)].

This acid was dissolved in EtOAc and treated with HCl gas as described for 2–9 to give pure 2–11.

$^1H$ NMR (400 MHz, $D_2O$) δ0.77 (3H, t), 1.16–1.33 (2H, m) 1.35–1.53 (2H, m), 1.55–1.63 (5H, m), 2.03 (2H, bd), 2.95 (2H, dt), 3.03–3.18 (4H, m), 3.41 (2H, bd), 3.52–3.65 (3H, m), 3.72 (2H, t), 3.92 (1H, dd), 4.34 (1H, dd), 7.94 (1H, s).

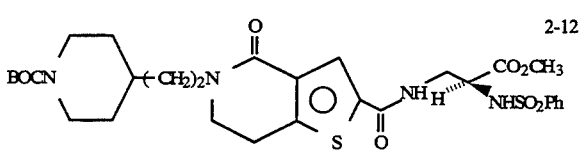

2-[3-(Methyl 2(S)-phenylsulfonylamino)propionate]carboxamide-4-oxo-5-[2-(N-BOC-4-piperidinyl)ethyl]-4,5,6,7-tetrahydro[3,2-c]pyridine (2–12)

2–5 (0.184 g, 0.45 mmoles) was treated with methyl 3-amino-2(S)phenylsulfonylaminopropionate (2–13) (0.13 f, 0.45 mmoles), HOBT (0.067 g, 0.5 mmoles) EDC (0.1 g, 0.52 mmoles) and NMM (0.14 g, 1.35 mmoles) as described for the preparation of 2–8 to give pure 2–12 after chromatography on silica gel eluting with $CHCl_3(95)/MeOH(5)$, $R_f$ 0.4.

$^1H$ NMR (300 MHz, $CDCl_3$) δ1.15 (2H, m), 1.31 (2H, m), 1.45 (9H, S), 1.55 (3H, m), 1.70 (2H, bd), 2.68 (2H, bt), 3.09 (2H, t), 3.60 (3H, S), 3.64 (3H, m), 3.82 (1H, m), 4.10 (2H, b), 7.45 (3H, m), 7.74 (1H, S), 7.82 (H, m).

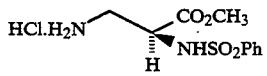

2(S)-(Phenylsulfonylamino)-3-aminopropionic acid methyl ester hydrochloride (2–13)

2–13 was prepared in similar fashion to 2–7, wherein phenylsulfonyl chloride was used as the sulfonylating agent.

$^1H$ NMR (300 MHz, $CD_3OD$) δ3.09 (1H, m), 3.30 (2H, m), 3.36 (1H, m), 3.40 (3H, S), 4.24 (1H, m), 7.60 (3H, m), 7.88 (2H, m).

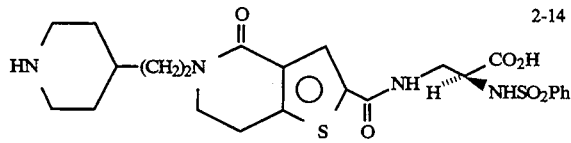

2-[3-(2(S)-Phenylsulfonylamino)propionic acid]carboxamide-4-oxo-5-[2-(4-piperidinyl)ethyl]-4,5,6,7-tetrahydro[3,2-c]pyridine (2-14)

2-12 was treated with LiOH.H₂O followed by HCl gas as described for 2-9 to give pure 2-14 as a white solid.

¹H NMR (400 mHz, D₂O) δ1.40–1.57 (2H, m), 1.60–1.74 (3H, m), 2.04 (2H, bd), 2.98 (2H, dt), 3.15 (2H, t), 3.35–3.49 (3H, m), 3.59 (2H, t), 3.70–3.83 (3H, m), 4.20 (1H, dd), 7.20–7.39 (4H, m), 7.71–7.78 (2H, m).

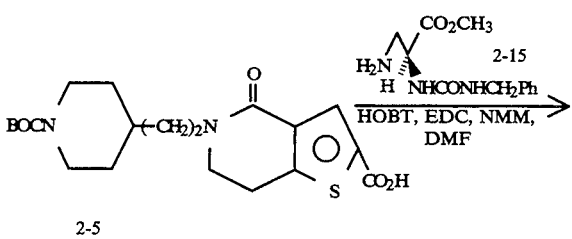

2-5

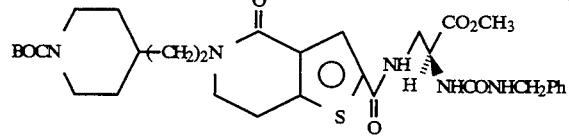

2-16

1. LiOH.H₂O
2. HCl (gas)/EtOAc

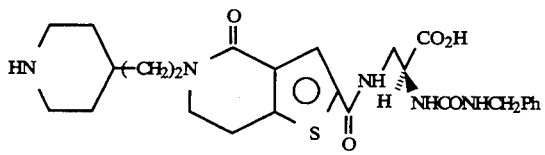

2-17

2-[3-(Methyl 2(S)-benzylureido)propionate]carboxamide-4-oxo-5-[2-(N-BOC-4-piperidinyl)ethyl]-4,5,6,7-tetrahydro[3,2-c]pyridine (2-16)

Treatment of 2-5 (0.16 g, 0.4 mmoles) with 2-15 (0.12 g, 0.42 mmoles), HOBT(0.06 g, 0.44 mmoles), EDC (0.1 g, 0.52 mmoles) and NMM (0.12 g, 1.2 mmoles) in DMF (20 ml) as described for 2-5 gave crude product. This was purified by flash chromatography on silica gel eluting with CHCl₃(97)/MeOH(3) to give pure 2-16, R_f 0.2.

¹H NMR (300 MHz, CDCl₃) δ1.12 (2H, m), 1.46 (9H, S), 1.68 (3H, m), 2.62 (2H, bt), 2.98 (2H, m), 3.40–3.65 (4H, m), 3.81 (3H, S), 4.07 (2H, m), 4.32 (2H, m), 4.63 (1H, m), 7.20 (4H, m), 7.78 (2H, m).

2-[3-(2(S)-benzylureido)propionic acid]carboxamide-4-oxo-5-[2-(4-piperidinyl)ethyl]-4,5,6,7-tetrahydro[3,2-c]pyridine (2-17)

Treatment of 2-16 (0.21 g, 0.326 mmoles) with LiOH.H₂O (0.041 g, 0.98 mmoles) in THF/MeOH/H₂O (1:1:1) as described for 2-8 gave the desired acid.

This acid was dissolved in EtOAc and treated with HCl gas as described for 2-9 to provide pure 2-17, R_f 0.25 [(silica, EtOH(10)/H₂O(1)/NH₄OH(1)].

¹H NMR (400 MHz, D₂O) δ1.35–1.49 (2H, m), 1.52–1.67 (3H, m), 1.98 (2H, bd), 2.90 (2H, dt) 3.06 (2H, t), 3.39 (2H, bd), 3.42–3.60 (2H, m), 3.63–3.77 (4H, m), 4.13 (1H, d), 4.31 (1H, d) 4.59 (1H, dd), 7.08–7.18 (5H, m), 7.60 (1H, S).

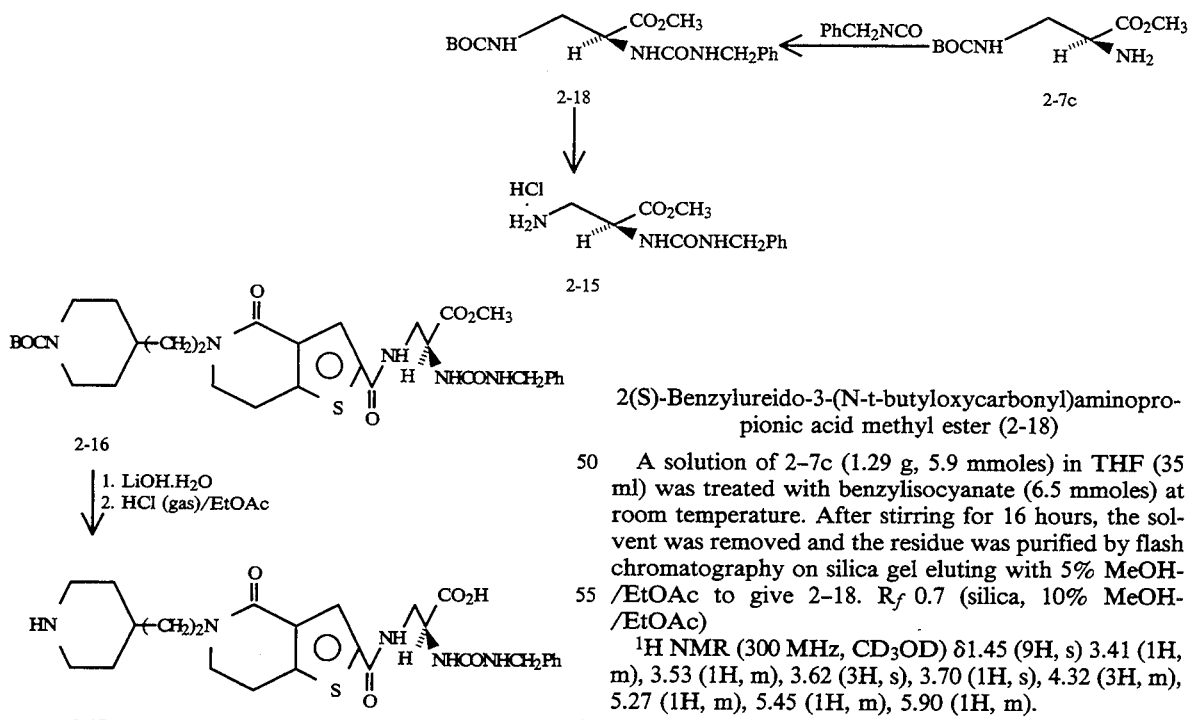

2(S)-Benzylureido-3-aminopropionic acid methyl ester hydrochloride (2-15)

2(S)-Benzylureido-3-(N-t-butyloxycarbonyl)aminopropionic acid methyl ester (2-18)

A solution of 2-7c (1.29 g, 5.9 mmoles) in THF (35 ml) was treated with benzylisocyanate (6.5 mmoles) at room temperature. After stirring for 16 hours, the solvent was removed and the residue was purified by flash chromatography on silica gel eluting with 5% MeOH/EtOAc to give 2-18. R_f 0.7 (silica, 10% MeOH/EtOAc)

¹H NMR (300 MHz, CD₃OD) δ1.45 (9H, s) 3.41 (1H, m), 3.53 (1H, m), 3.62 (3H, s), 3.70 (1H, s), 4.32 (3H, m), 5.27 (1H, m), 5.45 (1H, m), 5.90 (1H, m).

2(S)-Benzylureido-3-aminopropionic acid methyl ester hydrochloride (2-15)

Treatment of 2-18 (1.91 g) with HCl gas in EtOAc as described for 2-9 provided pure 2-15. R_f 0.66 (silica, 5% MeOH/CHCl₃/NH₃).

¹H NMR (300 MHz, CD₃OD) δ3.25 (1H, dd), 3.45 (1H, dd), 3.8 (3H, S), 4.4 (2H, S), 4.6 (1H, dd), 7.4 (5H, m).

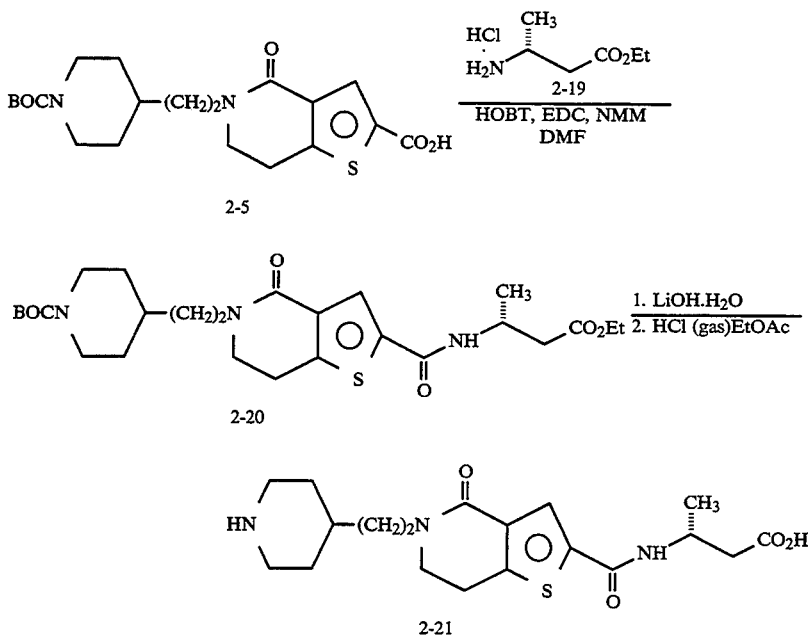

2-[3-(Ethyl 3(R)-methyl)propionate]carboxamide-4-oxo-5-[2-(N-BOC-4-piperidinyl)ethyl]-4,5,6,7-tetrahydrothieno[3,2-c]pyridine (2-20)

A solution of 2-5 (0.18 g, 0.45 mmoles) in DMF (15 ml) was treated successively with 2-19 (prepared according to the procedure for preparing compound 54 of European Publication 512,831, page 58, lines 16–42), HOBT (0.07 g, 0.5 mmoles), NMM (0.137 g, 1.35 mmoles) and EDC (0.1 g, 0.52 mmoles). After stirring at room temperature for 24 hours, the solvent was removed and the residue was taken up in $H_2O$/EtOAc and the organic phase was washed with 10% $KHSO_4$, brine, saturated $NaHCO_3$, brine, dried ($Na_2SO_4$) and concentrated to $R_f$0.45 [(silica, $CHCl_3$ (95)/MeOH(5)] give 2-20.

2-[3-(3(R)-Methyl)propionic acid]carboxamide-4-oxo-5-[2-(4-piperidinyl)ethyl]-4,5,6,7-tetrahydrothieno[3,2-c]pyridine (2-21)

2-20 (0.23 g, 0.44 mmoles) in THF/MeOH/$H_2O$ (1:1:1) (15 ml) was treated with LiOH.$H_2O$ (0.055 g, 1.32 mmoles) as described for 2-8 to provide the desired acid. $R_f$0.4 (silica, $CHCl_3$ (95)/MeOH(5).

This acid was dissolved in EtOAc and treated at −25° with HCl gas as described for 2-9 to give 2-21 as a white solid. $R_f$0.2 (silica, EtOH(10)/$NH_4OH$(1)/-$H_2O$(1)).

$^1$H NMR (400 MHz, $D_2O$) δ1.28 (3H, d), 1.33–1.50 (2H, m), 1.53–1.69 (3H, bm), 1.98 (2H, bd), 2.64 (2H, d), 2.94 (2H, dt) 3.11 (2H, bt), 3.39 (2H, bd), 3.45–3.59 (2H, bm), 3.70 (2H, bt), 4.43 (1H, m), 7.71 (1H, s).

SCHEME 3

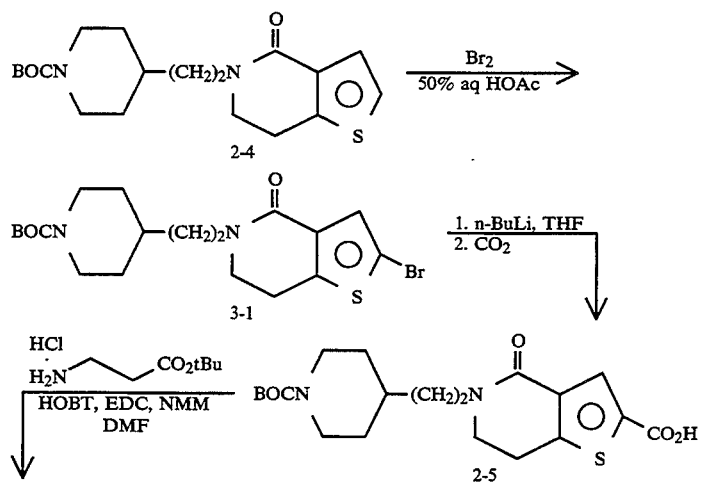

SCHEME 3

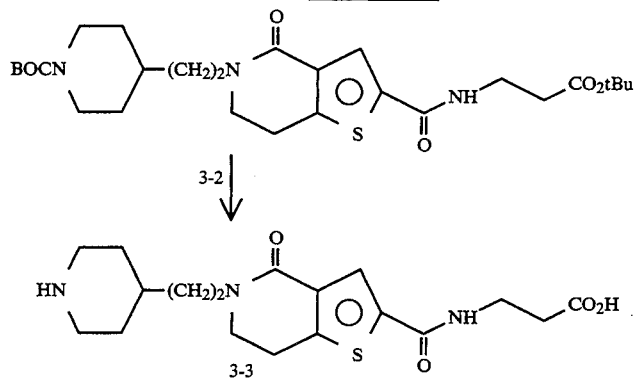

2-Bromo-4-oxo-5-[2-(N-BOC-4-piperidinyl)ethyl]-4,5,6,7-tetrahydrothieno[3,2-c]pyridine (3-1)

2-4 (0.73 g, 2.0 mmoles) was added to a 50% aqueous HOAc solution (40 ml) and after stirring at 0°–10° for 10 minutes, Br$_2$ (0.32 g, 2.0 mmoles) was added dropwise. After stirring at 0°–10° for 3 hours, the reaction mixture was diluted with 150 ml H$_2$O and extracted with EtOAc. The organic extract was washed with brine, dried (Na$_2$SO$_4$) and concentrated. The residue was purified by flash chromatography on silica gel eluting with hexane (85)/acetone (15) to give pure 3-1, R$_f$ 0.3.

$^1$H NMR (300 MHz, CDCl$_3$) δ1.14 (2H, m), 1.45 (9H, S), 1.50 (2H, m), 1.74 (2H, bd), 2.69 (2H, dt), 2.98 (2H, t), 3.48–3.64 (4H, m), 4.08 (2H, bd), 7.37 (1H, S).

2-Carboxy-4-oxo-5-[2-(N-BOC-4-piperidinyl)ethyl]-4,5,6,7-tetrahydrothieno[3,2-c]pyridine (2-5)

A solution of 2-18 (0.75 g, 1.7 mmoles) in THF (50 ml) was cooled to −78° and treated with n-BuLi. After stirring for 20 minutes the reaction mixture was poured into a stirred slurry of CO$_2$ in Et$_2$O and this was stirred for 30 minutes. The reaction mixture was then acidified with 10% KHSO$_4$ to pH 2–3 and extracted with EtOAc. The organic extract was washed with brine, dried (Na$_2$SO$_4$) and concentrated. The residue was purified by flash chromatgraphy on silica gel eluting with CHCl$_3$(97)/MeOH(2)/HOAc(1) to give pure 2-5, R$_f$ 0.4.

2-[3-(t-Butylpropionate)]carboxamide-4-oxo-5-[2-(N-BOC-4-piperidinyl)ethyl]-4,5,6,7-tetrahydrothieno[3,2-c]pyridine (3-2)

A solution of 2-5 (0.1 g, 0.25 mmoles) in DMF (10 ml) was treated with β-alanine hydrochloride t-butyl ester (0.05 g, 0.28 mmoles), HOBT (0.04 g, 0.3 mmoles), NMM (0.076 g, 0.75 mmoles) and EDC (0.06 g, 0.3 mmoles) and the resulting solution was stirred at room temperature for 16 hours. The solvent was removed, the residue was taken up in H$_2$O/EtOAc and the organic phase was washed with 10% KHSO$_4$, satd. NaHCO$_3$, brine, dried (Na$_2$SO$_4$) and concentrated. The crude residue was purified by flash chromatography on silica gel eluting with CHCl$_3$(95)/MeOH(5) to give pure 3-2, R$_f$ 0.45.

$^1$H NMR (300 MHz, CDCl$_3$) δ1.15 (2H, m), 1.45 (18H, S), 1.51 (3H, m), 2.73 (2H, bd), 2.52 (2H, d), 2.69 (2H, dt), 3.09 (2H, t), 3.54 (2H, t), 3.64 (2H, m), 4.07 (2H, bd), 7.71 (1H, S).

2-[3-(Propionic acid)]carboxamide-4-oxo-5-[2-(piperidinyl)]ethyl-4,5,6,7-tetrahydrothieno[3,2-c]pyridine (3-3)

A solution of 3-2 (0.12 g) in EtOAc at −25° was treated with HCl gas as described for 2-9 to provide pure 3-3 as a white solid, R$_f$ 0.25 [(silica, EtOH(10)/H$_2$O(1)/NH$_4$OH(1)].

$^1$H NMR (300 mHz, CD$_3$OD) δ1.33–1.55 (2H, m) 1.55–1.73 (3H, m), 2.05 (2H, bd), 2.61, (2H, t), 2.95 (2H, dt), 3.14 (2H, t), 3.38 (2H, bd), 3.50–3.68 (4H, m), 3.72 (2H, t), 7.72 (1H, S), 8.63 (½H, bt).

SCHEME 4

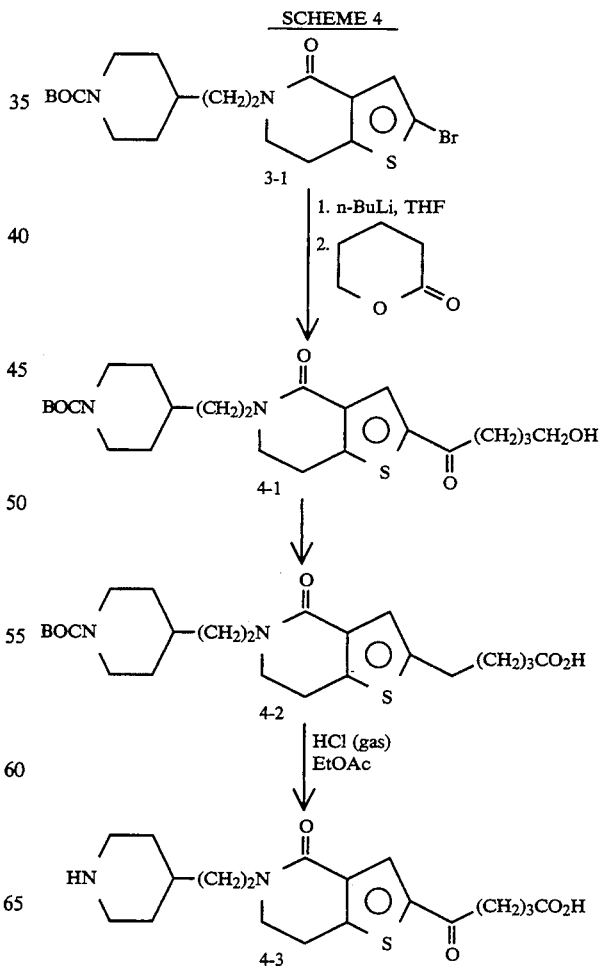

2-(5-Hydroxypentanoyl)-4-oxo-5-[2-(N-BOC-4-piperidinyl)ethyl-]4,5,6,7-tetrahydrothieno[3,2-c]pyridine (4-1)

A solution of 3-1 (0.66 g, 1.5 mmoles) in THF (30 ml) was cooled to −78° and treated with n-BuLi (3.0 mmoles) and the resulting yellow brown solution was stirred for 30 minutes. Then, valerolactone (0.16 g, 1.65 mmoles) was added and this was stirred at −70° for 6 hours and then overnight at ambient temperature. The reaction mixture was cooled to −10°, quenched with 10% KHSO₄ and concentrated. The residue was taken up in H₂O/EtOAc and the organic phase was washed with brine, dried (Na₂SO₄) and concentrated. The residue was purified by flash chromatography on silica gel eluting with hexane (3)/acetone(2) to give 4-1, R$_f$ 0.35.

2-(5-Carboxypentanoyl)-4-oxo-5-[2-N-BOC-4-piperidinyl)ethyl]-4,5,6,7-tetrahydrothieno[3,2-c]pyridine (4-2)

A solution of 4-1 in acetone was cooled to 0°–10° and treated with excess Jones reagent. After stirring for 1 hour the reaction mixture was diluted with H₂O/EtOAc and the organic phase was separated washed with H₂O, brine, dried (Na₂SO₄) and concentrated. The residue was purified by flash chromatography on silica gel eluting with CDCl₃(97)/MeOH(2.5)/HOAc(0.5) to give pure 4-2, R$_f$ 0.4.

¹H NMR (300 MHz, CDCl₃) δ1.15 (2H, m), 1.45 (9H, S), 1.56 (3H, m), 1.73 (2H, bd), 2.08 (2H, m), 2.49 (2H, t), 2.69 (2H, dt), 3.00 (2H, t), 3.10 (2H, t), 3.55 (2H, t), 3.64 (2H, t), 4.09 (2N, bd), 8.05 (1H, S).

2-(5-Carboxypentanoyl)-4-oxo-5-[2-(4-piperidinyl)ethyl]-4,5,6,7-tetrahydrothieno[3,2-c]pyridine (4-3)

4-2 (0.083 g, 0.173 mmoles) was dissolved in EtOAc, cooled to −25°, and treated with HCl gas as described for 2–9 to give pure 4-3, R$_f$ 0.5 [(silica, MeOH(10)/NH₄OH(1)/H₂O(1)].

1H NMR (400 mHz, D₂O) δ1.38-1.52 (2H, m), 1.56-1.70 (3H, bm), 1.90-2.06 (4H, m), 2.46 (2H, t), 2.88-3.08 (4H, m), 3.15 (2H, bt), 3.40 (2H, bd), 3.49-3.60 (2H, bm), 3.72 (2H, bt), 7.98 (1H, bs).

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

Using methods described herein, as well as others that are known in the literature, the following compounds may be prepared and are descriptive of the present invention:

TABLE 1

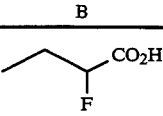

| X | Y | Z | E | D | A | B |
|---|---|---|---|---|---|---|
| CH₃NH— | CH₂ | CH₂ | CH | S | $\overset{O}{\underset{}{\overset{\|}{C}}}$NH | 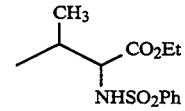 |
| H₂NCNH— (NH) | CNH (O) | (C₂H₅)₃ | S | CH | NHC (O) | 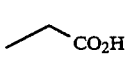 |
| CH₃NHCNH— (NH) | OCH₃ / CN | CH=CH | NH | CH | (CH₂)₂ |  |
| 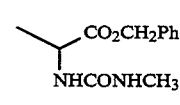 HN | NHC (O) | CH=C— (CH₃) | CH | NCH₃ | C(CH₂)₂ (O) | 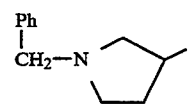 |
| 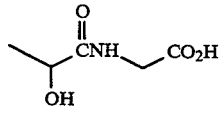 Ph–CH₂–N | C (O) | —CH₂C— (O) | O | CH | CH₂C (O) | 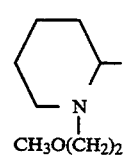 |
| 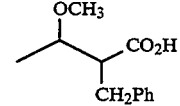 N–CH₃O(CH₂)₂ | C (S) | C—CH— (O Ph) | CH | O | SO₂N(CH₃) | OCH₃ / CO₂H / CH₂Ph |

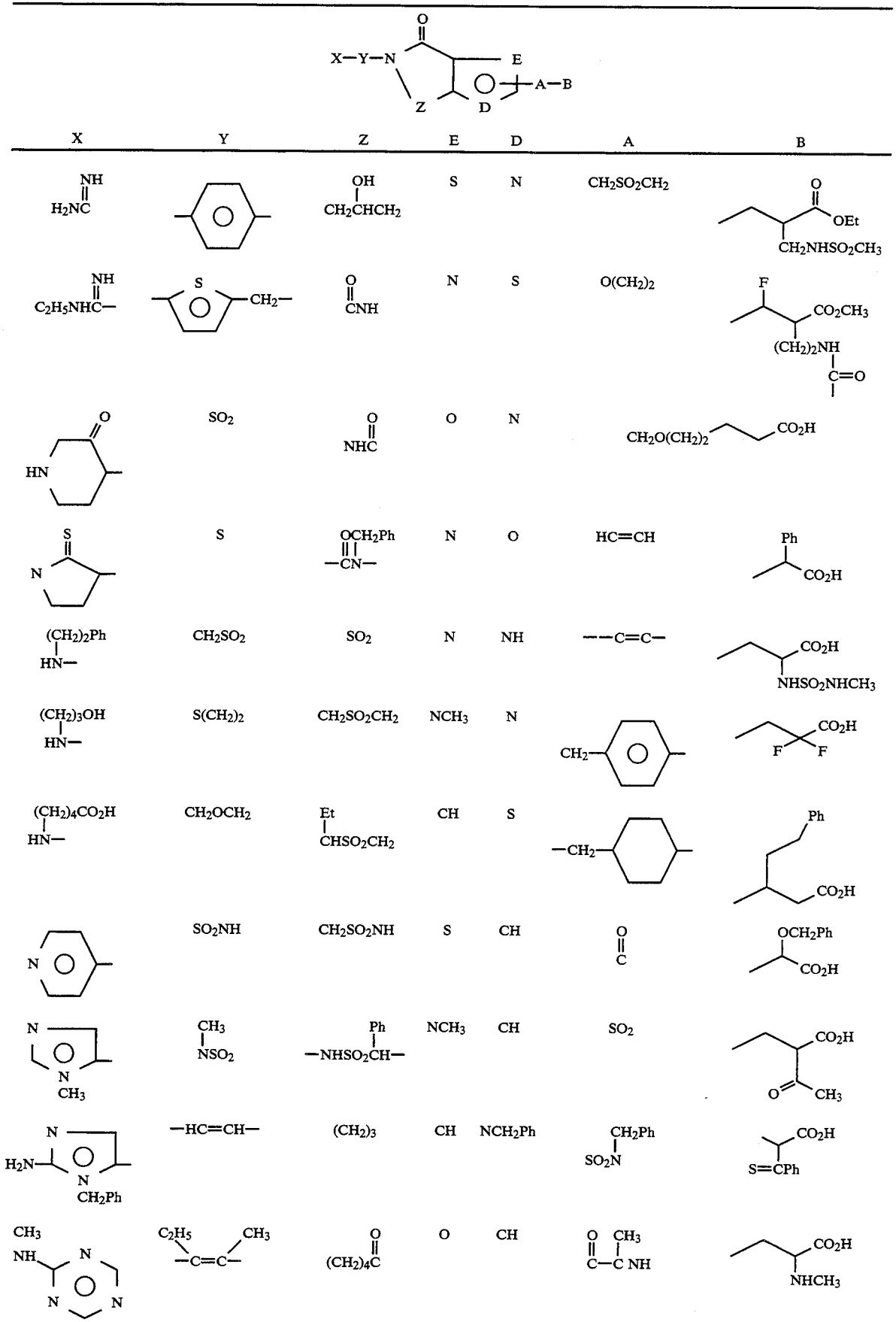

TABLE 1-continued

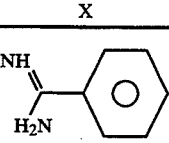

| X | Y | Z | E | D | A | B |
|---|---|---|---|---|---|---|
| (NH/H2N-phenyl amidine) | —C≡C— | SO₂(CH₂)₂ | CH | O | (CH₂)₃ | NHCH₃ / CH(CH₃)CO₂H |
| (H2N-thiazole-CH=) | (N=C(CH₃)- cyclohexyl-CH₂) | CH₂—C(OEt)=N— | S | N | CH₂SO₂ | CH(CH₃)-C(F)(O)NH-CH(CH₂Ph)CO₂CH₃ |
| (H2N-methylpyridine) | —CH₂-phenyl- | —C(CH₃)=N— | N | S | CH₂-(tetrahydrofuran) | CH(CH(CH₃)₂)(CO₂H)(CH₂OC(O)NH₂) |

What is claimed is:

1. A compound having the formula

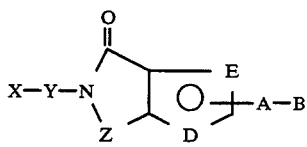

and pharmaceutically acceptable salts, wherein
X is a 6-membered non-aromatic ring with 0 to 1 N atoms;
Y is $(CH_2)_m$, where m is an integer from 0–6;
Z is $(CH_2)_2$;
D is O or S;
E is C;
A is

wherein n is 1 or 2;
B is chosen from

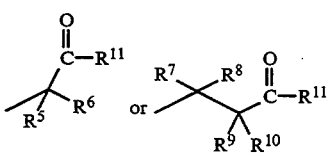

where
$R^3$ is H, $C_{1-10}$ alkyl or aryl $C_{0-8}$alkyl;
$R^5$ is H;
$R^6$ is independently chosen from substituted or unsubstituted: hydrogen, fluorine,
$C_{1-8}$ alkyl, hydroxyl, hydroxy $C_{1-6}$ alkyl, carboxy $C_{0-6}$ alkyl,
$C_{1-6}$ alkyloxy, $C_{1-6}$ alkylcarbonyl, aryl $C_{0-6}$ alkylcarbonyl,
$C_{1-6}$ alkylcarbonyloxy, aryl $C_{0-6}$ alkylcarbonyloxy,
$C_{1-6}$ alkylaminocarbonyloxy, aryl$C_{0-6}$alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl, and
aryl $C_{0-6}$ alkylthiocarbonylamino $C_{0-6}$ alkyl,
  wherein groups may be unsubstituted or substituted with one or more substituents selected from hydrogen,
  $C_{1-10}$ alkyl,
  aryl $C_{0-8}$ alkyl,
  oxo,
  thio,
  amino $C_{0-8}$ alkyl, $C_{1-3}$ acylamino $C_{0-8}$ alkyl,
  $C_{0-6}$ alkylamino $C_{0-8}$ alkyl,
  $C_{1-6}$ dialkylamino $C_{0-8}$ alkyl,
  $C_{1-4}$ alkoxy $C_{0-6}$ alkyl,
  carboxy $C_{0-6}$ alkyl, $C_{1-3}$ alkoxycarbonyl $C_{0-6}$ alkyl,
  carboxy $C_{0-6}$ alkyloxy, and
  hydroxy $C_{0-6}$ alkyl,
and

where G is an L- or D-amino acid, or its corresponding ester, connected through an amide linkage;
$R^7$ is H or $CH_3$;
$R^8$ is H or $CH_3$;
$R^9$ is H;
$R^{10}$ is independently chosen from substituted or unsubstituted: hydrogen, fluorine,
$C_{1-8}$ alkyl, hydroxyl, hydroxy $C_{1-6}$ alkyl, carboxy $C_{0-6}$ alkyl,
$C_{1-6}$ alkyloxy, $C_{1-6}$ alkylcarbonyl, aryl $C_{0-6}$ alkylcarbonyl,
$C_{1-6}$ alkylcarbonyloxy, aryl $C_{0-6}$ alkylcarbonyloxy, $C_{1-6}$ alkylaminocarbonyloxy, aryl$C_{0-6}$alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl, and
aryl $C_{0-6}$ alkylthiocarbonylamino $C_{0-6}$ alkyl,
wherein groups may be unsubstituted or substituted with one or more substituents selected from hydrogen,
$C_{1-10}$ alkyl,
aryl $C_{0-8}$ alkyl,
oxo,
thio,
amino $C_{0-8}$ alkyl, $C_{1-3}$ acylamino $C_{0-8}$ alkyl,
$C_{0-6}$ alkylamino $C_{0-8}$ alkyl,
$C_{1-6}$ dialkylamino $C_{0-8}$ alkyl,
$C_{1-4}$ alkoxy $C_{0-6}$ alkyl,
carboxy $C_{0-6}$ alkyl, $C_{1-3}$ alkoxycarbonyl $C_{0-6}$ alkyl,
carboxy $C_{0-6}$ alkyloxy, and
hydroxy $C_{0-6}$ alkyl,
and

where G is an L- or D-amino acid, or its corresponding ester, connected through an amide linkage; and
$R^{11}$ is chosen from
hydroxy,
$C_{1-8}$ alkyloxy,
aryl $C_{0-6}$ alkyloxy,
$C_{1-8}$ alkylcarbonyloxy $C_{1-4}$ alkyloxy, and
aryl $C_{1-8}$ alkylcarbonyloxy $C_{1-4}$ alkyloxy, or
an L- or D-amino acid joined by an amide linkage and wherein the carboxylic acid moiety of said amino acid is as the free acid or is esterified by $C_{1-6}$ alkyl.

2. A compound of claim 1, wherein
$R^6$ is independently chosen from substituted or unsubstituted: hydrogen, fluorine,
$C_{1-8}$ alkyl, hydroxyl, hydroxy $C_{1-6}$ alkyl, carboxy $C_{0-6}$ alkyl,
$C_{1-6}$ alkyloxy, $C_{1-6}$ alkylcarbonyl, aryl $C_{0-6}$ alkylcarbonyl,
$C_{1-6}$ alkylcarbonyloxy, aryl $C_{0-6}$ alkylcarbonyloxy, $C_{1-6}$ alkylaminocarbonyloxy, aryl$C_{0-6}$alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl, and
aryl $C_{0-6}$ alkylthiocarbonylamino $C_{0-6}$ alkyl,
wherein groups may be unsubstituted or substituted with one or more substituents selected from hydrogen,
$C_{1-10}$ alkyl,
aryl $C_{0-8}$ alkyl,
oxo, and
thio,
and

where G is an L- or D- amino acid, or its corresponding ester, connected through an amide linkage;
$R^{10}$ is independently chosen from substituted or unsubstituted: hydrogen, fluorine,
$C_{1-8}$ alkyl, hydroxyl, hydroxy $C_{1-6}$ alkyl, carboxy $C_{0-6}$ alkyl,
$C_{1-6}$ alkyloxy, $C_{1-6}$ alkylcarbonyl, aryl $C_{0-6}$ alkylcarbonyl,
$C_{1-6}$ alkylcarbonyloxy, aryl $C_{0-6}$ alkylcarbonyloxy, $C_{1-6}$ alkylaminocarbonyloxy, aryl$C_{0-6}$alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl, aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl, and
aryl $C_{0-6}$ alkylthiocarbonylamino $C_{0-6}$ alkyl,
wherein groups may be unsubstituted or substituted with one or more substituents selected from hydrogen,
$C_{1-10}$ alkyl,
aryl $C_{0-8}$ alkyl,
oxo, and
thio,
and

where G is an L- or D- amino acid, or its corresponding ester, connected through an amide linkage;
$R^{11}$ is chosen from
hydroxy,
$C_{1-8}$ alkyloxy,
aryl $C_{0-6}$ alkyloxy,
$C_{1-8}$ alkylcarbonyloxy $C_{1-4}$ alkyloxy, and
aryl $C_{1-8}$ alkylcarbonyloxy $C_{1-4}$ alkyloxy.

3. A compound of claim 2, wherein
D is S;
$R^6$ is independently chosen from substituted or unsubstituted:
hydrogen, fluorine,
$C_{1-8}$ alkyl, hydroxyl, hydroxy $C_{1-6}$ alkyl, carboxy $C_{0-6}$ alkyl,
$C_{1-6}$ alkyloxy, $C_{1-6}$ alkylcarbonyl, aryl $C_{0-6}$ alkylcarbonyl,
$C_{1-6}$ alkylcarbonyloxy, aryl $C_{0-6}$ alkylcarbonyloxy, $C_{1-6}$ alkylaminocarbonyloxy, aryl$C_{0-6}$alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl, and
aryl $C_{0-6}$ alkylthiocarbonylamino $C_{0-6}$ alkyl,
wherein groups may be unsubstituted or substituted with one or more substituents selected from hydrogen,
$C_{1-10}$ alkyl, and
aryl $C_{0-8}$ alkyl,
and

where G is an L- or D- amino acid, or its corresponding ester, connected through an amide linkage;
$R^{10}$ is independently chosen from substituted or unsubstituted:
hydrogen, fluorine,
$C_{1-8}$ alkyl, hydroxyl, hydroxy $C_{1-6}$ alkyl, carboxy $C_{0-6}$ alkyl,
$C_{1-6}$ alkyloxy, $C_{1-6}$ alkylcarbonyl, aryl $C_{0-6}$ alkylcarbonyl,
$C_{1-6}$ alkylcarbonyloxy, aryl $C_{0-6}$ alkylcarbonyloxy, $C_{1-6}$ alkylaminocarbonyloxy, aryl$C_{0-6}$alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl, and
aryl $C_{0-6}$ alkylthiocarbonylamino $C_{0-6}$ alkyl,
wherein groups may be unsubstituted or substituted with one or more substituents selected from hydrogen,
$C_{1-10}$ alkyl, and
aryl $C_{0-8}$ alkyl,
and

where G is an L- or D-amino acid, or its corresponding ester, connected through an amide linkage.

4. A compound of claim 1 selected from the group consisting of:

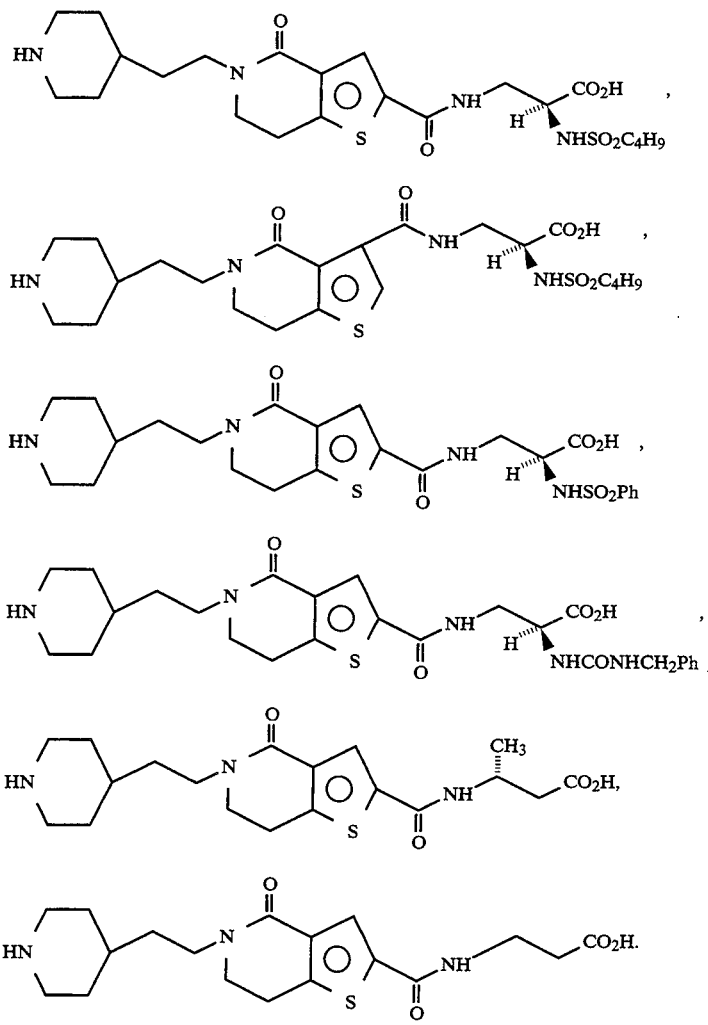

5. A compound of claim 1 for use in inhibiting the binding of fibrinogen to blood platelets, inhibiting the aggregation of blood platelets, or treating thrombus formation or embolus formation, in a mammal.

6. A composition for inhibiting the binding of fibrinogen to blood platelets in a mammal, comprising a compound of claim 1 and a pharmaceutically acceptable carrier.

7. A composition for inhibiting the aggregation of blood platelets in a mammal, comprising a compound of claim 1 and a pharmaceutically acceptable carrier.

8. A composition for treating thrombus or embolus formation in a mammal, comprising a compound of claim 1 and a pharmaceutically acceptable carrier.

9. A method for inhibiting the binding of fibrinogen to blood platelets in a mammal, comprising administering to the mammal a composition of claim 7.

10. A method for inhibiting the aggregation of blood platelets in a mammal, comprising administering to the mammal a composition of claim 7.

11. A method for treating thrombus or embolus formation in a mammal, comprising administering to the mammal the composition of claim 8.

12. A compound of claim 4 for use in inhibiting the binding of fibrinogen to blood platelets, inhibiting the aggregation of blood platelets, or treating thrombus formation or embolus formation in a mammal.

13. A composition for inhibiting the binding of fibrinogen to blood platelets, in a mammal, comprising a compound of claim 4 and a pharmaceutically acceptable carrier.

14. A composition for inhibiting the aggregation of blood platelets, in a mammal, comprising a compound of claim 4 and a pharmaceutically acceptable carrier.

15. A composition for treating thrombus or embolus formation in a mammal, comprising a compound of claim 4 and a pharmaceutically acceptable carrier.

16. A method for inhibiting the binding of fibrinogen to blood platelets in a mammal, comprising administering to the mammal a composition of claim 14.

17. A method for inhibiting the aggregation of blood platelets in a mammal, comprising administering to the mammal a composition of claim 14.

18. A method for treating thrombus or embolus formation in a mammal, comprising administering to the mammal a composition of claim 15.

* * * * *